(12) United States Patent
North

(10) Patent No.: US 8,685,040 B2
(45) Date of Patent: Apr. 1, 2014

(54) SHAPED ELECTRODE AND DISSECTING TOOL

(76) Inventor: Richard B. North, Baltimore, MD (US)

( * ) Notice: Subject to any disclaimer, the term of this patent is extended or adjusted under 35 U.S.C. 154(b) by 310 days.

(21) Appl. No.: 12/838,559

(22) Filed: Jul. 19, 2010

(65) Prior Publication Data

US 2011/0015646 A1 Jan. 20, 2011

Related U.S. Application Data

(60) Provisional application No. 61/226,392, filed on Jul. 17, 2009.

(51) Int. Cl.
*A61B 19/00* (2006.01)

(52) U.S. Cl.
USPC ........... 606/129; 600/377; 600/378; 607/116; 607/119; 606/222; 606/223; 604/164.06; 604/170.01

(58) Field of Classification Search
USPC .......... 606/129; 600/372–374, 377, 378, 379, 600/394; 607/116, 119
See application file for complete search history.

(56) References Cited

U.S. PATENT DOCUMENTS

| | | | |
|---|---|---|---|
| 4,010,756 A * | 3/1977 | DuMont et al. | 607/132 |
| 4,244,375 A * | 1/1981 | Farrar et al. | 600/373 |
| 4,407,302 A | 10/1983 | Hirshorn et al. | |
| 4,467,800 A | 8/1984 | Zytkovicz | |
| 4,735,208 A * | 4/1988 | Wyler et al. | 600/377 |
| 4,841,971 A | 6/1989 | Hess | |
| 4,919,135 A | 4/1990 | Phillips, Jr. et al. | |
| 5,036,854 A * | 8/1991 | Schollmeyer et al. | 600/374 |
| 5,486,173 A | 1/1996 | Vancaillie | |
| 5,582,610 A | 12/1996 | Grossi et al. | |
| 6,135,999 A | 10/2000 | Fanton et al. | |
| 6,203,540 B1 | 3/2001 | Weber | |
| 6,308,103 B1 | 10/2001 | Gielen | |
| 6,734,425 B2 | 5/2004 | Hantschel et al. | |
| 7,321,798 B2 | 1/2008 | Muhlenberg et al. | |
| 7,489,971 B1 | 2/2009 | Franz | |
| 7,708,733 B2 | 5/2010 | Sanders et al. | |
| 7,736,330 B2 | 6/2010 | Bardy | |
| 7,824,398 B2 | 11/2010 | Woloszko et al. | |
| 2003/0130655 A1 * | 7/2003 | Woloszko et al. | 606/45 |
| 2003/0199962 A1 | 10/2003 | Struble et al. | |
| 2005/0021118 A1 * | 1/2005 | Genau et al. | 607/116 |
| 2009/0247823 A1 | 10/2009 | Yamamoto | |

FOREIGN PATENT DOCUMENTS

| | | |
|---|---|---|
| WO | WO2006015131 | 2/2006 |
| WO | WO2010118312 | 10/2010 |

* cited by examiner

*Primary Examiner* — Katherine Dowe
*Assistant Examiner* — Sidharth Kapoor
(74) *Attorney, Agent, or Firm* — Whiteford, Taylor & Preston, LLP; Gregory M. Stone

(57) ABSTRACT

Disclosed is a shaped electrode and dissecting tool configured to aid in controlling the path of an electrode as it is moved into its intended position within the epidural space of a patient. The shaped electrode and dissecting tool is configured with a contoured leading edge having at least one concavity that aids in moving the electrode and dissecting tool through the intended tissues within the patient's body. A variety of concavity contours may be provided and used for particular surgical applications.

16 Claims, 5 Drawing Sheets

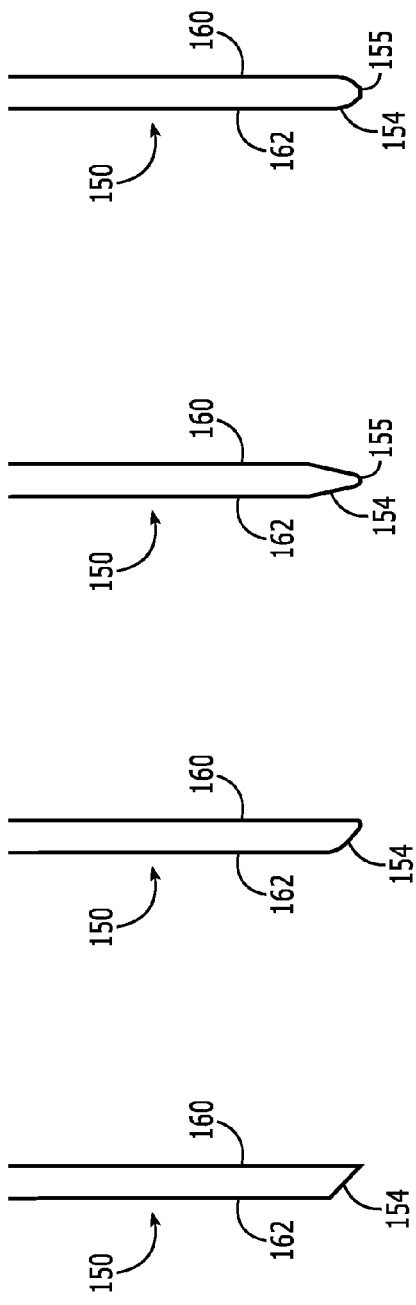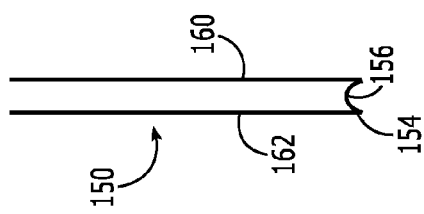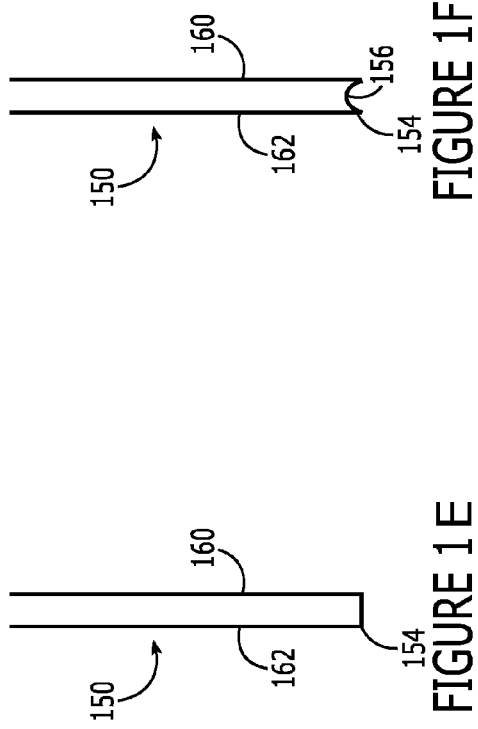

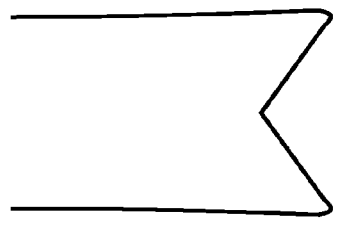
FIGURE 2A
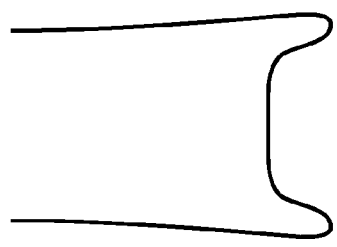
FIGURE 2B
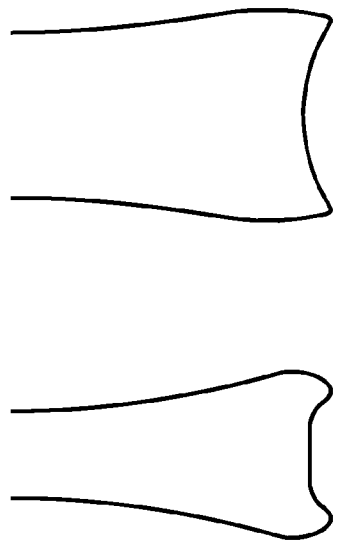
FIGURE 2C
FIGURE 2D
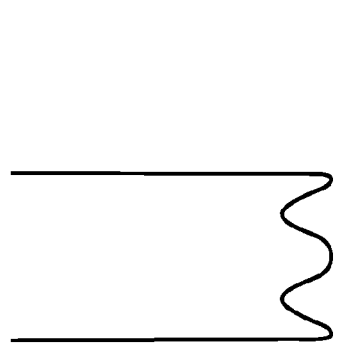
FIGURE 2E
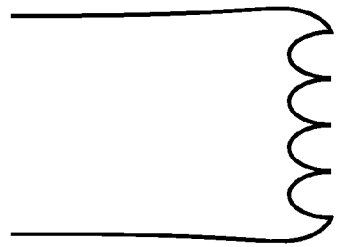
FIGURE 2F
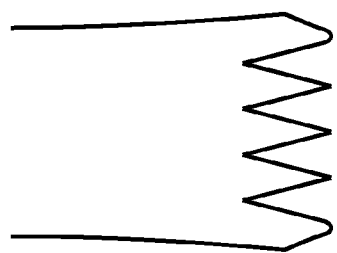
FIGURE 2G
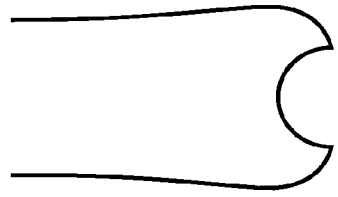
FIGURE 2H

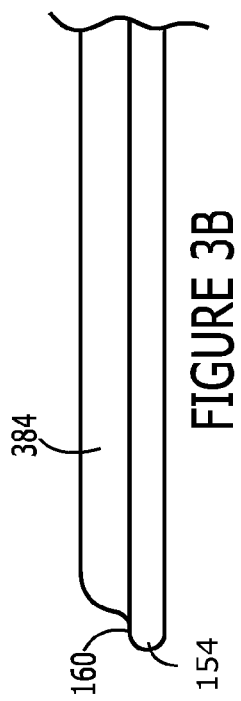
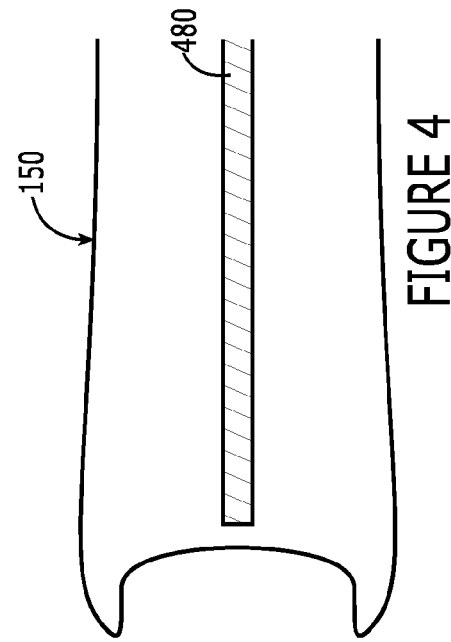
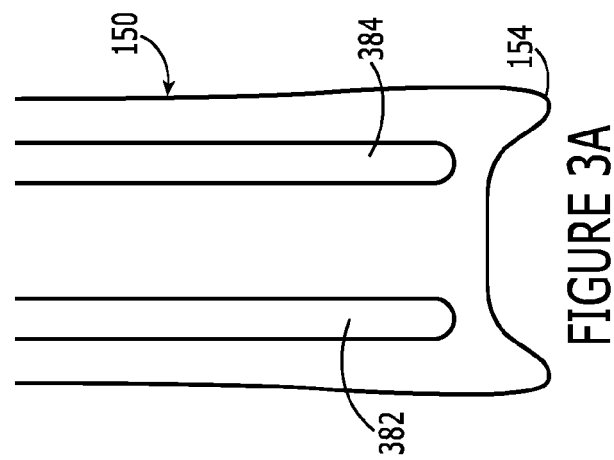

SHAPED ELECTRODE AND DISSECTING TOOL

CROSS REFERENCE TO RELATED APPLICATION

This application is based upon and claims benefit of copending U.S. Provisional Patent Application Ser. No. 61/226,392 entitled "Shaped Electrode and Dissecting Tool", filed with the U.S. Patent and Trademark Office on Jul. 17, 2009 by the inventor herein, the specification of which is incorporated herein by reference.

FIELD OF THE INVENTION

The present invention relates generally to the field of implantable medical electronic devices, such as electrical stimulators, epidural electrodes, defibrillators and pacemakers, and more particularly to a shaped electrode and a tool for placing electrodes and similar devices that provides greater control while inserting within a tissue plane, such as the spinal (or cranial) epidural space or the subcutaneous space.

BACKGROUND OF THE INVENTION

Implantable medical devices ("IMD") are used today for various applications to deliver electrical pulses from a pulse generator within the IMD, through an electrical lead connected to the IMD, to a targeted location within a patient's body. For example, IMD's may be used in neurological applications, such as for deep-brain stimulation and spinal cord simulation, in which leads deliver electrical pulses generated in the IMD through the electrical lead to targeted portions of a patient's brain or spinal cord. In still other applications, leads may be used to sense particular conditions within a patient's body, and relay that sensed condition back to a processing unit within the IMD.

The electrodes extending from such IMD's are typically introduced through a needle or surgical opening (e.g., a laminectomy or laminotomy) into the epidural space. As they are advanced, it is generally preferable that they proceed in direct contact with the dura, so as to be close to the spinal cord, rather than through the fatty tissue behind the dura, which not only add electrical resistance but also add mechanical resistance. The forces resisting electrode advancement, as the electrode traverses spaces and tissues with different properties, are highly variable. Moreover, fibrous webs and scar tissue, for example, may block the intended path for the electrode, and they may cause the electrode to deviate to one side or the other, or dorsally and away from the dura, and away from the intended path.

Such difficulty in placement of the electrodes creates challenges for the operator, as appropriate electrode positioning is quite important to ensure proper delivery of the intended treatment. The appropriate position for the electrode may be determined by test stimulation, typically in the aware patient, who reports areas of the body where stimulation elicits paresthesia. Thus, one goal of electrode implantation is to achieve the proper distribution of paresthesia by adjusting the left-right and longitudinal position of the electrode. Test stimulation may be delivered intermittently, while the electrode is stationary, rather than continuously. Representative contact combinations may be tested if a multicontact electrode is used. Unfortunately, this process of determining proper electrode placement may be quite time consuming.

In other cases, electrodes may be placed to achieve appropriate radiographic electrode position. Percutaneous electrodes, for example, are routinely positioned under continuous, real-time fluoroscopy, which allows them to be steered as they are advanced in the epidural space. Likewise, insulated paddle electrodes can be positioned under fluoroscopy. In each of these cases, physically steering the electrode to its intended position may be a challenging and tedious process.

In still other cases, electrodes may be placed under direct vision, such as where an electrode is placed via laminectomy. In this case, the dura is directly visualized through a surgical opening, and the electrode is placed through the opening. Typically, the size of the electrode exceeds the size of the opening, and it is advanced through the opening, ascending or descending through the epidural space beneath intact lamina (e), concealing it from view. To the extent that the visible portion of the electrode is connected physically to the invisible portion, the position of the latter must typically be inferred.

In each of these cases, the configuration of the electrode, and particularly of paddle electrodes, makes them difficult to manipulate and control as they are directed to their intended implantation site. More particularly, paddle electrodes typically (i) have limited torsional and bending rigidity, (ii) are difficult to grasp and hold with standard surgical instruments; and (iii) by virtue of their shape and size may respond inconsistently to manipulation. As a result of these issues, they become unwieldy as the tip of the electrode is advanced away from the bony opening.

In order to aid in the placement of such devices, electrode manufacturers may supply "blanks" that are the same size and shape as the electrode, and that may be introduced before the electrode, in order to confirm that the exposure is adequate and that the path for the electrode is clear. Some such blanks may be soft and supple, while others may be relatively rigid (more so than the electrode), and may be used as dissecting tools to open and define the space as necessary. Such blanks and dissecting tools that may be supplied with SCS electrodes unfortunately carry similar disadvantages to those discussed above with regard to the electrodes themselves, and may themselves experience difficulty when meeting an obstruction in the epidural space. There is often a septum of fibrous tissue in the midline of the normal epidural space, and patients who have had previous surgery, epidural injections, and epidural catheter or electrode placement may have epidural scarring. Standard instruments, like standard electrodes, having a rounded tip may, when they encounter an obstruction, deviate to one side or the other, again making control difficult. Even under fluoroscopy, and even with a relatively rigid instrument or electrode, this can be intractable and frustrating for the operator.

It would therefore be desirable to provide an improved electrode, as well as a dissecting and/or electrode placement tool, wherein the design or configuration of the tool itself provides a mechanism that facilitates the process of implantation.

SUMMARY OF THE INVENTION

Disclosed is a shaped electrode and dissecting tool configured to aid in controlling the path of an electrode as it is moved into its intended position within the epidural space of a patient. Whether used as an electrode or as a tool for placement of an electrode or other implantable medical device, the tool comprises a tip having a leading edge that is configured to aid in moving the tool. More specifically, the leading edge is provided one or more concavities extending into the tip, which concavities may comprise generally rounded indentations, sawtooth configurations, or combinations thereof with either curved or sharp edges to accommodate various applications. In addition to being provided such concave contours, the leading edge itself may be configured with a chisel-shaped or pointed edge to further aid in movement of the tool during the surgical procedure.

With regard to a particularly preferred embodiment of the invention, such an electrode or tool is provided that comprises a tip having a first end and a second end opposite the first end, the second end defining the leading edge of the tip, and a shaft attached to the first end of said tip (which shaft may be, for instance, a handle for manipulating the head of a placement tool, or alternatively the electrical cable leading from the electrode back to, for instance, an implantable electrical pulse generator), wherein the leading edge of the tip further comprises at least one concave notch extending into the tip from the second end of the tip.

BRIEF DESCRIPTION OF THE DRAWINGS

The numerous advantages of the present invention may be better understood by those skilled in the art by reference to the accompanying drawings in which:

FIGS. 1A-1F are illustrations of different configurations for the profile of the tip of the tool or electrode of FIG. 1;

FIGS. 2A-2H are illustrations of different concavity contours for the tip of the tool or electrode of FIG. 1;

FIGS. 3A and 3B are illustrations of a two-keeled tip of a tool or electrode in accordance with an exemplary embodiment of the current invention;

FIG. 4 is an illustration of a grooved tip of a tool or electrode in accordance with an exemplary embodiment of the current invention;

DETAILED DESCRIPTION OF THE INVENTION

The following description is of a particular embodiment of the invention, set out to enable one to practice an implementation of the invention, and is not intended to limit the preferred embodiment, but to serve as a particular example thereof. Those skilled in the art should appreciate that they may readily use the conception and specific embodiments disclosed as a basis for modifying or designing other methods and systems for carrying out the same purposes of the present invention. Those skilled in the art should also realize that such equivalent assemblies do not depart from the spirit and scope of the invention in its broadest form.

With regard to a particularly preferred embodiment of the invention, an improved electrode and a tool for placement of such an electrode is provided, each of which includes a shaped leading edge that promotes increased control during the process of implanting within a tissue plane, and preferably within a spinal epidural space, of a patient. Generally, the leading edge of the electrode or tool is notched to include one or more concavities along the surface of the edge which may come in contact with obstructions within the epidural space of a patient as the electrode or tool is advanced. The concave surface(s) may provide an operator with increased control over the direction or path taken during the implantation process. Whereas convex or even flat surfaces may tend to glance off of obstructions (e.g., adhesions) in the tissue plane, the concavity(ies) engage them and allow the tool to traverse them as the operator retains directional control.

Generally, the use of the term "tool" shall be understood to refer to items such as a dissector, dissecting tool, blank, instrument, electrode, or any such other commonly used device for the placement of electrodes into a tissue plane, such as the epidural space. Thus, the description provided herein below shall be understood to apply to any and all such devices, instruments or tools without limitation. Any alternative embodiments as known to those skilled in this field of technology shall fall within the scope and spirit of the current invention.

Figure 1:
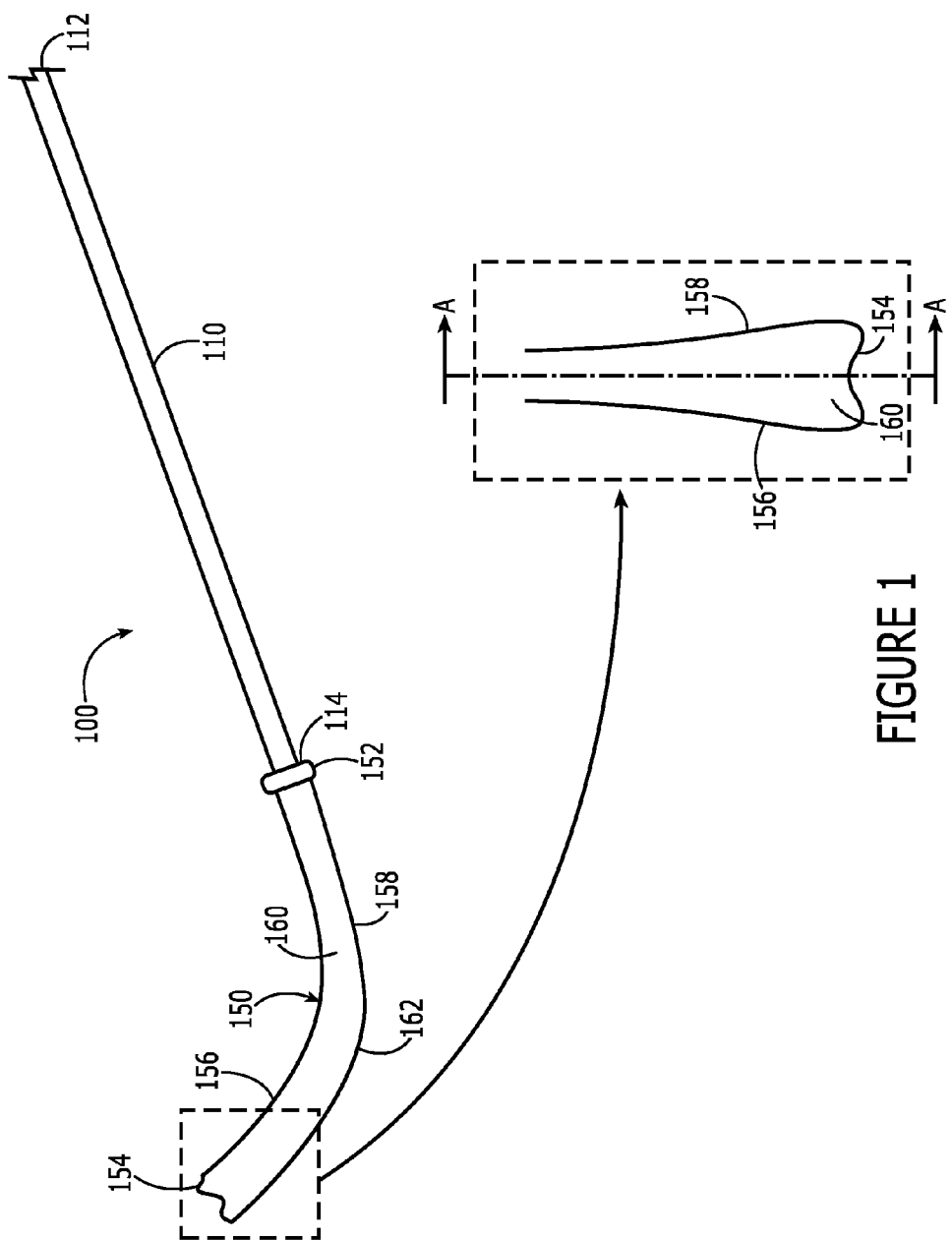
FIG. 1 is an illustration of an electrode and a dissecting tool used for the placement of an electrode in accordance with an exemplary embodiment of the current invention.

With particular reference to FIG. 1, a tool 100 is shown including a shaft 110 integrally formed with a tip 150, the tip 150 configured in such a manner as to promote increased control of the tool during the insertion and positioning (implantation) of an electrical stimulation device (e.g., an electrode) within an epidural space of a patient. The shaft 110 may be of customary and sufficient length to allow the tool 100 to be inserted in the proper position within the patient to perform its function. The length of the shaft 110 is defined by a first end 112 and a second end 114. In the current embodiment, the second end 114 is integrally connected with a first end 152 of the tip 150. A second end 154 of the tip 150 is referred to herein as the "leading edge" of the tool 100. The second end 154 is the first part of tool 100 to come in contact with an obstruction during the implantation process.

In the current embodiment, the shaft 110 is integrally connected with the tip 150. Alternative embodiments contemplate that the connection between the shaft and tip may allow retro-fitting or the interchanging of different shafts and/or tips with one another. Various connection technologies may be employed to provide this interchangeable capability, such as compression lock mechanisms, quick-connect mechanisms, threaded connection mechanisms, friction-fit connection mechanisms, and others as may be contemplated by those skilled in the art.

Preferably, the overall length of the tool may range from 6 to 12 inches, and is more preferably 10 inches as shown in the current embodiment. It is contemplated that the overall length of the tool may be less than 6 inches or greater than 12 inches for use in different regions of the body, or in patients of different sizes. The shaft 110 may be formed of various length and thickness dimensions. In the current embodiment the shaft 110 may be 8 inches long and formed in a generally cylindrical shape. Alternatively, the shaft may be configured in a square shape, triangular shape or various other shapes. The thickness of the shaft, as determined by the diameter of the cylindrical shaft in the current embodiment, is preferably 2 to 5 millimeters and is constant from the first end 112 to the second end 114. The thickness (diameter or otherwise) may also be varied ranging from less than 1 millimeter to greater than 4 millimeters or as contemplated by those skilled in the art. The varying thickness may provide greater rigidity or flexibility to the tool and thereby impact upon the performance of the tool during the implantation process.

In the current, particularly preferred embodiment, the tip 150 is generally configured in a rectangularly or trapezoidally shaped body defined by the second end ("leading edge") 154, first side 156, second side 158, top side 160, bottom side 162 and the first end 152. The overall length of the tip 150, from first end 152 to second end 154, may preferably range between 1½ and 3½ inches, and is more preferably 2½ inches. It is contemplated that the tip length may vary from less than 1½ inches to greater than 3½ inches without departing from the scope and spirit of the current invention. The overall width of the tip 150 as defined by the distance between first side 156 and second side 158 may preferably range between 8 and 14 millimeters.

The thickness of tip 150 is selected to promote its stability during the implantation process, and as such, any necessary thickness may be provided for tip 150 as is contemplated by those skilled in the art. Generally, the thickness of the tip may range from 1 to 3 millimeters between a top side 160 and bottom side 162; however, the thickness may vary for the overall length of the tip or for certain sections of the tip.

The leading edge 154 may be configured to provide a desired sharpness to tip 150. This is important as the leading edge 154 is configured to promote the guidance of the tool as it passes through the epidural space and may encounter various obstructions that must be overcome. The sharpness of the leading edge 154 may be varied and the angle(s) of incidence from the leading edge may be established relative to either the top side 160, the bottom side 162 or both, so as to maximize the effectiveness of tool 100 in traversing the epidural space, and so as to influence its direction. As spinal epidural space commonly contains fatty tissue, configuring the tip 150 so that in side view it constitutes an asymmetric wedge or chisel shape may facilitate directing the tool up or down as it advances. For example, as shown in FIG. 1A, tip 150 may be configured with a chisel-shaped leading edge 154 in which top side 160 extends further along the length of tip 150 than bottom side 162, with leading edge 154 creating an angled surface (when viewed in cross-section as shown in FIG. 1A). In the exemplary embodiment of FIG. 1A, the edge surfaces at which leading edge 154 meets top side 160 and bottom side 162 may form a relatively sharp edge, thus aiding in allowing tip 150 to traverse through fatty tissue in the patient. Alternatively, and particularly with regard to FIG. 1B, leading edge may be provided in a similar chisel-shaped configuration but with radiused or slightly rounded edge surfaces at which leading edge 154 meets top side 160 and bottom side 162. As another alternative, and particularly with regard to FIG. 1C, the thickness of leading edge 154 may narrow to a point 155, in which case both top edge 160 and bottom edge 162 converge toward one another as they approach the free end of tip 150. As shown in FIG. 1C, tip 150 may be relatively sharp. Alternatively, and as shown in FIG. 1D, tip 150 may be provided with a rounded point 155, in which case the edge surfaces where leading edge 154 meets top side 160 and bottom side 162, along with tip 150, are radiused or curved to provide a generally rounded point 155.

While any of the foregoing configurations may be desirable for particular applications, leading edge 154 may likewise be provided with no sharpened or chisel-shaped contour, as shown in FIG. 1E, and likewise may be provided a convex face 155A (when viewed in cross-section as shown in FIG. 1F) to aid in navigating through the intended tissue in the patient.

In a preferred embodiment, electrode placement ventral to the fatty tissue and in direct contact with the dura is desirable, and so the wedge may be configured with its apex or tip closer to the ventral than the dorsal surface. In another embodiment, the wedge is configured with its apex closer to the dorsal surface to direct it upward, as would be useful for example in passing the tip between the inner surface of the skull and the dura, directing the tip away from the brain. As shown in FIGS. 1A through 1F, the tip of the instrument as seen in side view may be configured so as to be relatively sharp or blunt as appropriate to the application.

In the current embodiment, at least a portion of the leading edge 154 is formed with one or more concavity(ies) as seen in plan view. The specific dimensions that form the concavity may vary as contemplated by those of ordinary skill in the art so as to maximize the effectiveness of the tool 100 in traversing the epidural space.

The concavity of leading edge 154 may terminate at its edges in radiused corners, which is the angular dimension of the point where the leading edge 154 meets with either the first side 156 or the second side 158. In preferred, exemplary embodiments, the radius is sufficiently small to maintain a relatively sharp corner, and the angle defining the concavity of leading edge 154 may be an acute angle, an arc, or combinations thereof. However, the specific radius dimensions provided may vary between different embodiments of the invention.

An important dimensional feature for the tool 100 is that of the angles or curves creating one or more notches in the leading edge 154 of the tip 150, and various configurations of the leading edge 154 of the tip 150 are shown in FIGS. 2A through 2H. Various single-concavity configurations are shown in FIGS. 2A, 2B, 2C and 2H. Alternative configurations include a sawtooth configuration with varying numbers of teeth, as shown in FIGS. 2E, 2F, and 2G. The depth of each tooth and angular dimensions (lateral and vertical) for the point and edges of each tooth may be varied as may be required by or desirable for particular applications. Further, various polygonal or polygonal-based shapes, such as the "V" shaped example of FIG. 2D, may likewise be employed without departing from the scope and spirit of the instant invention.

The tool or electrode may be constructed so that the user may modify it in the field by trimming or cutting away portions of the tip, so as to facilitate directing it, for example to the right or the left.

With regard to another aspect of a particularly preferred embodiment of the invention, tip 150 is shown in FIGS. 3A and 3B including a first keel 382 and a second keel 384 that are positioned along the length of the tip 150 on the top side 160. The height and length of the keels may vary. In the current embodiment, the keels run nearly the entire length of the top side 160 of the tip 150 and have a height preferably ranging from 0.5 to 1 millimeter, and more preferably 0.75 millimeter. In alternative embodiments the keel(s) may extend only a part of the length of the top side, such as halfway down the length of the top side.

It is contemplated that the number of keels provided may vary, such as only including one or three or more. Further, the dimensions of the keels may be consistent throughout or may vary between different sections. The keels, as shown, are disposed only along the top side; in the alternative the keels may be disposed along the bottom side or keels may be disposed on both the top and bottom side of the same tip.

In another exemplary embodiment, the tip 150 shown in FIG. 4 is provided with a groove 480 that promotes the flexibility of the tip 150 to fold upon itself during the insertion through and into an epidural space. The groove, 480 is established in the top side, but may be established in the bottom side of the tip 150. The depth of the groove may vary but shall always be less than the thickness of the tip. The width of the groove may vary but shall always be less than the width of the tip. The folding capability promoted by the groove, in combination with the shaped second end of the tip provides further direction control during the insertion of the tip into an epidural space.

Figure 5:
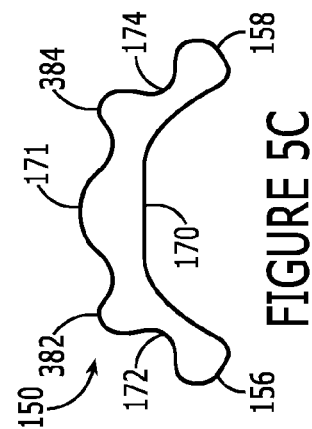
FIG. 5 is a top view and FIGS. 5A-5C are cross-sectional views of a tool or electrode in accordance with another aspect of a particularly preferred embodiment of the invention.
Figure 5A:
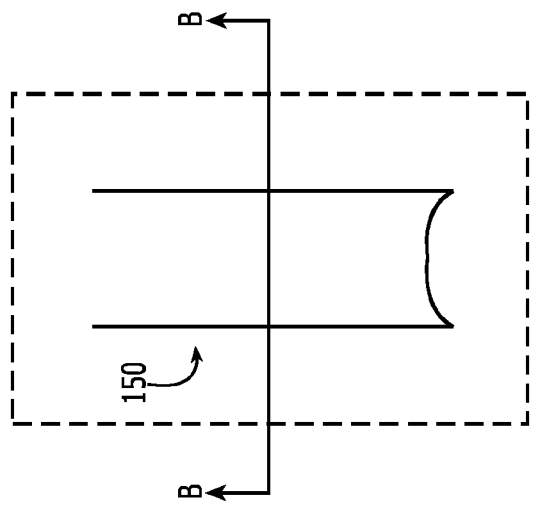
Figure 5B:
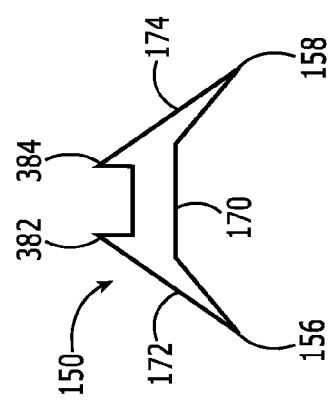
Figure 5C:
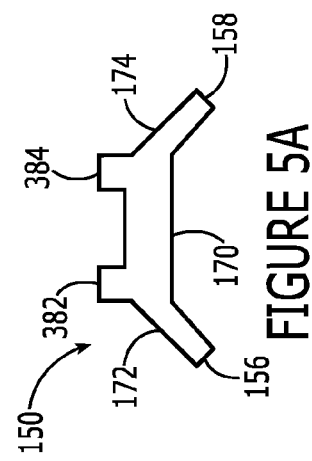

Next, with regard to the exemplary embodiment shown in FIG. 5, the cross-section of the tool or electrode may be folded or angled, in polygonal fashion, so as to conform to the shape of the tissue plane in which it is inserted. The dorsal epidural space of the spine, for example, is not flat; it may be represented by three or more adjacent surfaces, each at an angle with respect to the next, so as to conform to its shape in three dimensions. Thus, and with particular regard to FIG. 5A, tip 150 may be provided a flat midsection 170, a first angled face 172 extending downward from the flat midsection 170 to first side 156, and a second angled face 174 extending downward from the flat midsection 170 to second side 158, with keels 382 and 384 positioned on the top of flat midsection 170. Similarly, and as shown in FIG. 5B, tip 150 may be provided a flat midsection 170, a first angled face 172 extending downward from the flat midsection 170 to first side 156 and reducing in thickness to a thin edge at first side 156, and a second angled face 174 extending downward from the flat midsection 170 to a second side 158 and reducing in thickness to a thin edge at second side 158. Once again, keels 382 and 384 may be positioned on the top of flat midsection 170, and optionally may themselves reduce in thickness to a point so as to form a thin edge along the tip of each of keels 382 and 384. Still further, and with reference to FIG. 5C, tip 150 may be provided a midsection 170 having a convex top face 171, a first angled face 172 extending downward from midsection 170 to first side 156 and having a rounded, convex edge at first side 156, and a second angled face 174 extending downward from midsection 170 to a second side 158 and having a rounded, convex edge at second side 158. Again, keels 382 and 384 may be positioned on the top of midsection 170, and may themselves form rounded, convex edges at their upper extent and concave edges where they intersect with midsection 170 and angled faces 172 and 174, thus maintaining a smooth and generally continuously rounded contour for the outer perimeter of tip 150.

It shall be understood that various other characteristics of the novel tool of the current invention may be changed without departing from the spirit and scope of the present invention. For instance, the material composition of the tool may comprise plastic, metal, or other materials, so long as such material is biologically inert. The material composition of the shaft of the tool may be similar to or different from that of the tip. Moreover, different sections or pieces of the shaft and/or tip may be similar or of different material composition from one another. In addition, while the exemplary embodiments show a tool with a shaft and/or tip of constant proportion and configuration throughout, it is contemplated that either or both parts of the tool may include varying proportions or configurations.

It is believed that the present invention and many of its attendant advantages will be understood by the forgoing description. It is also believed that it will be apparent that various changes may be made in the form, construction and arrangement of the components thereof without departing from the spirit and scope of the invention or without sacrificing all of its material advantages. The form herein before described is merely an explanatory embodiment thereof.

I claim:

1. A tool for placing an implantable medical electronic device within the body of a patient, the tool comprising:
    an implantable electrode having a proximal and a distal end;
    a tip positioned at the distal end of the implantable electrode, wherein the tip comprises
        a first end and a second end opposite said first end, said second end defining a leading edge of said tip, wherein said leading edge further comprises at least one concave notch extending into said tip from said second end of said tip, a top face extending from said second end toward said first end of said tip, a bottom face extending from said second end toward said first end of said tip and parallel to said top face, a first side edge between said top face and said bottom face, and a second side edge between said top face and said bottom face and extending parallel to said first side edge, wherein said first and second side edges define a thickness dimension of said tip, wherein a longitudinal length dimension of said top face and said bottom face is several times greater than said thickness dimension, and wherein said top face, bottom face, first side edge and second side edge of said tip together form a flat, rectangular paddle;
        said tip further comprising at least one of a keel or a groove extending longitudinally along said tip for at least half of said length dimension of said top face; and
    a shaft attached to said first end of said tip.

2. The tool of claim 1, further comprising a plurality of concave notches extending into said tip from said second end of said tip.

3. The tool of claim 2, wherein said plurality of concave notches form a sawtooth arrangement along said leading edge.

4. The tool of claim 1, wherein said at least one concave notch comprises an inverted v-shaped notch extending into said tip from said second end of said tip.

5. The tool of claim 1, wherein said top face extends a greater length from said first end of said tip than said bottom face, such that said leading edge forms a generally chisel-shaped tip having a tapering thickness as it approaches the second end of said tip.

6. The tool of claim 5, wherein edges at which said leading edge intersects said top face and said bottom face comprise rounded edges.

7. The tool of claim 1, wherein edges at which said leading edge intersects said first side edge and said second side edge are convex edges.

8. The tool of claim 1, wherein said keel or groove extends longitudinally along said top face of said tip.

9. The tool of claim 8, further comprising a plurality of keels situated on said top face.

10. The tool of claim 1, wherein the depth of said groove is less than the full thickness of said tip.

11. The tool of claim 1, said tip further comprising a flat midsection, a first angled face extending downward at said first side edge from said flat midsection, and a second angled face extending downward at said second side edge from said flat midsection.

12. The tool of claim 11, wherein said keel is situated on said top face at a top side of said flat midsection.

13. The tool of claim 12, wherein said first angled face is reduced in thickness as it extends away from said flat midsection, and said second angled face is reduced in thickness as it extends away from said flat midsection.

14. The tool of claim 13, wherein said keel is reduced in thickness as it extends away from said top side of said flat midsection.

15. The tool of claim 1, wherein said shaft attached to said first end of said tip is removable.

16. The tool of claim 1, wherein said tip has a shape that conforms with a tissue plane in which said tip is to be inserted.

* * * * *